United States Patent
Villongco et al.

(10) Patent No.: US 12,213,742 B2
(45) Date of Patent: Feb. 4, 2025

(54) ABLATION TARGETING AND PLANNING SYSTEM

(71) Applicant: The Vektor Group Inc., San Diego, CA (US)

(72) Inventors: Christopher J. T. Villongco, Oakland, CA (US); Christian David Marton, Jersey City, NJ (US); Robert Joseph Krummen, Bellevue, WA (US)

(73) Assignee: THE VEKTOR GROUP, INC., San Diego, CA (US)

( * ) Notice: Subject to any disclaimer, the term of this patent is extended or adjusted under 35 U.S.C. 154(b) by 0 days.

(21) Appl. No.: 18/631,049

(22) Filed: Apr. 10, 2024

(65) Prior Publication Data

US 2024/0341852 A1     Oct. 17, 2024

Related U.S. Application Data

(60) Provisional application No. 63/627,047, filed on Jan. 30, 2024, provisional application No. 63/496,366, filed on Apr. 14, 2023.

(51) Int. Cl.
*A61B 34/10* (2016.01)
*A61B 18/02* (2006.01)
(Continued)

(52) U.S. Cl.
CPC ............ *A61B 34/10* (2016.02); *A61B 18/02* (2013.01); *G16H 10/60* (2018.01); *G16H 40/63* (2018.01);
(Continued)

(58) Field of Classification Search
CPC .......... A61B 18/02; A61B 2018/00531; A61B 2018/00577; A61B 2018/00702;
(Continued)

(56) References Cited

U.S. PATENT DOCUMENTS 10,319,144 B2    6/2019   Krummen et al.
10,402,966 B2    9/2019   Blake, III
(Continued)

FOREIGN PATENT DOCUMENTS

WO    2022165245 A1    8/2022

OTHER PUBLICATIONS

Dosovitskiy, A., et al., An Image is Worth 16X16 Words: Transformers for Image Recognition at Scale, Published as a confernce paper at ICLR 2021, 22 pages.
(Continued)

*Primary Examiner* — Khadijeh A Vahdat
(74) *Attorney, Agent, or Firm* — Perkins Coie LLP

(57) ABSTRACT

A system is provided for generating an ablation plan for an ablation procedure to be performed on a body part of a patient having an abnormal pattern of electrical activity. The system receives patient data that includes a patient cardiogram, a patient body part image; and patient health data. The system employs an ablation target system to identify an ablation target within the body part based on at least some of the patient data. The system also employs an ablation plan system to identify, based on at least some of the patient data and the ablation target, an ablation plan that includes target parameter values for ablation device parameters for controlling an ablation device. The ablation plan system is developed based on data that includes data sets with patient data associated with an ablation plan. The system then outputs an indication of the ablation target and the ablation plan.

19 Claims, 12 Drawing Sheets

(51) Int. Cl.
  *G16H 10/60*    (2018.01)
  *G16H 40/63*    (2018.01)
  *A61B 18/00*    (2006.01)
(52) U.S. Cl.
  CPC ............. *A61B 2018/00351* (2013.01); *A61B 2018/00577* (2013.01); *A61B 2018/00702* (2013.01); *A61B 2018/00761* (2013.01); *A61B 2034/104* (2016.02); *A61B 2034/107* (2016.02)
(58) Field of Classification Search
  CPC .......... A61B 2018/00761; A61B 34/10; A61B 2034/107; G16H 10/60
  See application file for complete search history.

(56) References Cited

U.S. PATENT DOCUMENTS

| | | | |
|---|---|---|---|
| 10,734,096 | B1* | 8/2020 | Neumann ................ G06N 7/01 |
| 10,856,816 | B2 | 12/2020 | Villongco |
| 10,925,511 | B2 | 2/2021 | Blake et al. |
| 11,259,871 | B2 | 3/2022 | Villongco |
| 2014/0022250 | A1 | 1/2014 | Mansi et al. |
| 2017/0027649 | A1* | 2/2017 | Kiraly .................... A61B 90/37 |
| 2017/0220754 | A1 | 8/2017 | Harrah et al. |
| 2019/0328457 | A1* | 10/2019 | Villongco .............. G16H 10/60 |
| 2020/0022649 | A1* | 1/2020 | Rodriguez ........... A61B 5/4878 |
| 2021/0137384 | A1* | 5/2021 | Robinson .................. G06T 7/10 |
| 2021/0272297 | A1 | 9/2021 | Chen et al. |
| 2022/0008126 | A1 | 1/2022 | Tsoref et al. |
| 2022/0192749 | A1 | 6/2022 | Villongco et al. |

OTHER PUBLICATIONS

Fayyad, U. M., et al., "On the Handling of Continuous-Valued Attributes in Decision Tree Generation," Machine Learning, 1992, 16 pages, vol. 8, Kluwer Academic Publishers, Boston.

Villongco, Christopher T., et al. "Patient-specific modeling of ventricular activation pattern using surface ECG-derived vectorcardiogram in bundle branch block." Progress in biophysics and molecular biology 115.2 (2014): 305-313.

Vaswani, A., Shazeer, N., Parmar, N., Uszkoreit, J., Jones, L., Gomez, A.N., Kaiser, Ł. and Polosukhin, I., 2017. Attention is all you need. Advances in neural information processing systems, 30.

Gu, A. and Dao, T., 2023. Mamba: Linear-time sequence modeling with selective state spaces. arXiv preprint arXiv:2312.00752 (Mamba).

International Search Report and Written Opinion received for Application No. PCT/US24/23763, mailed on Sep. 19, 2024, 18 pages.

* cited by examiner

ABLATION TARGETING AND PLANNING SYSTEM

CROSS-REFERENCE TO RELATED APPLICATIONS

This application claims the benefit of the U.S. Application No. 63/496,366, filed on Apr. 14, 2023, and the benefit of the U.S. Application No. 63/627,047, filed on Jan. 30, 2024, the entire disclosure of each of these applications is incorporated herein by reference.

BACKGROUND

Many heart disorders can cause adverse symptoms, morbidity (e.g., syncope or stroke), and mortality. Common heart disorders caused by arrhythmias include inappropriate sinus tachycardia ("IST"), ectopic atrial rhythm, junctional rhythm, ventricular escape rhythm, atrial fibrillation ("AF"), ventricular fibrillation ("VF"), focal atrial tachycardia ("focal AT"), atrial microreentry, ventricular tachycardia ("VT"), atrial flutter ("AFL"), premature ventricular complexes ("PVCs"), premature atrial complexes ("PACs"), atrioventricular nodal reentrant tachycardia ("AVNRT"), atrioventricular reentrant tachycardia ("AVRT"), permanent junctional reciprocating tachycardia ("PJRT"), and junctional tachycardia ("JT"). The sources of arrhythmias may include electrical rotors (e.g., ventricular fibrillation), recurring electrical focal sources (e.g., atrial tachycardia), anatomically based reentry (e.g., ventricular tachycardia), and so on. These sources are important drivers of sustained or clinically significant episodes. Arrhythmias can be treated with ablation using different technologies, including radiofrequency energy ablation, cryoablation, ultrasound ablation, laser ablation, external radiation sources, directed gene therapy, pulsed electric fields, and so on by targeting the source of the heart disorder. Since the sources of heart disorders and the locations of the source vary from patient to patient, even for common heart disorders, targeted therapies require the source of the arrhythmia to be identified.

In some situations, an arrhythmia may be treated by targeting a location other than the source location of an arrhythmia. For example, an AF may be caused by an activation that is originated at a source location that is at the root of a pulmonary vein (PV). The standard of care for treating a patient with an AF with a source location that is near the root is a pulmonary vein isolation (PVI). Rather than targeting the source location of the AF, a PVI (as its name suggests) isolates the PV by ablating a target region of myocardial cells that encircle the PV. The ablated myocardial cells are unable to propagate action potential, which means the action potential activated at the root of the PV cannot pass through the ablated myocardial cells to activate the other myocardial cells of the atrium. As a result, normal sinus rhythm is not interrupted by the activation at the source location, and the AF is terminated.

Some PVIs may not be completely effective because some of the myocardial cells within the target regions are still able propagate action potential. Those myocardial cells can propagate action potential because, for example, the contact of the ablation device with those myocardial cells was not sufficient to kill them or otherwise disrupt their function. Those myocardial cells form a gap in the target region through which action potential (originating at the root of the PV) can propagate to other myocardial cells of the atrium resulting in an arrhythmia. In addition, even if a PVI is initially completely effective, over time myocardial cells may grow within the ablated region also causing a gap that allows action potential to propagate through the ablated region. Regardless of how a gap is formed, a subsequent ablation would target the gap rather than the source location or the entire original target region.

Machine learning and non-machine learning techniques may be used to identify the source location of an arrhythmia. Such techniques are described in U.S. Pat. No. 10,856,816 entitled "Machine Learning using Simulated Cardiogram" and issued on Dec. 8, 2020, and U.S. Pat. No. 10,319,144 entitled "Computational Localization of Fibrillation Source" and issued on Jun. 11, 2019, which are hereby incorporated by reference. However, in certain situations, an ablation should target a region other than the source location. Such situations include when there is an ablation gap in a prior ablation or when the source location may be difficult to reach or is near a critical structure (e.g., sinoatrial node or a nerve). Although knowledge of the source location is helpful in planning a procedure, current technologies may not effectively identify a region that should be the target of the ablation in these situations.

Regardless of whether the target is the source location or another location, the effectiveness of an ablation is based at least in part on the settings of tunable parameters of the ablation device used in the ablation procedure. Ablation devices include radiofrequency ablation devices, pulsed field ablation devices, cryoablation devices, stereotactic ablative therapy devices, irreversible electroporation devices, and so on. These ablation devices have different device characteristics and tunable parameters. The device characteristics include device type (e.g., pulsed field), manufacturer, model number, and so on. The tunable parameters have parameters values that can be specified for an ablation procedure. For example, the tunable parameters may include wattage, current, frequency, pulse shape, pulse duration, pulse frequency, contact force, balloon size, electrode size and spacing, electrode orientation, impedance, hoop diameter, fluence, and so on. The selection of effective parameter values can help reduce the time needed to perform an ablation, minimize the number of ablations during a procedure, and improve the outcome of an ablation procedure such as reducing the need for a subsequent ablation.

DETAILED DESCRIPTION

Figure 1:
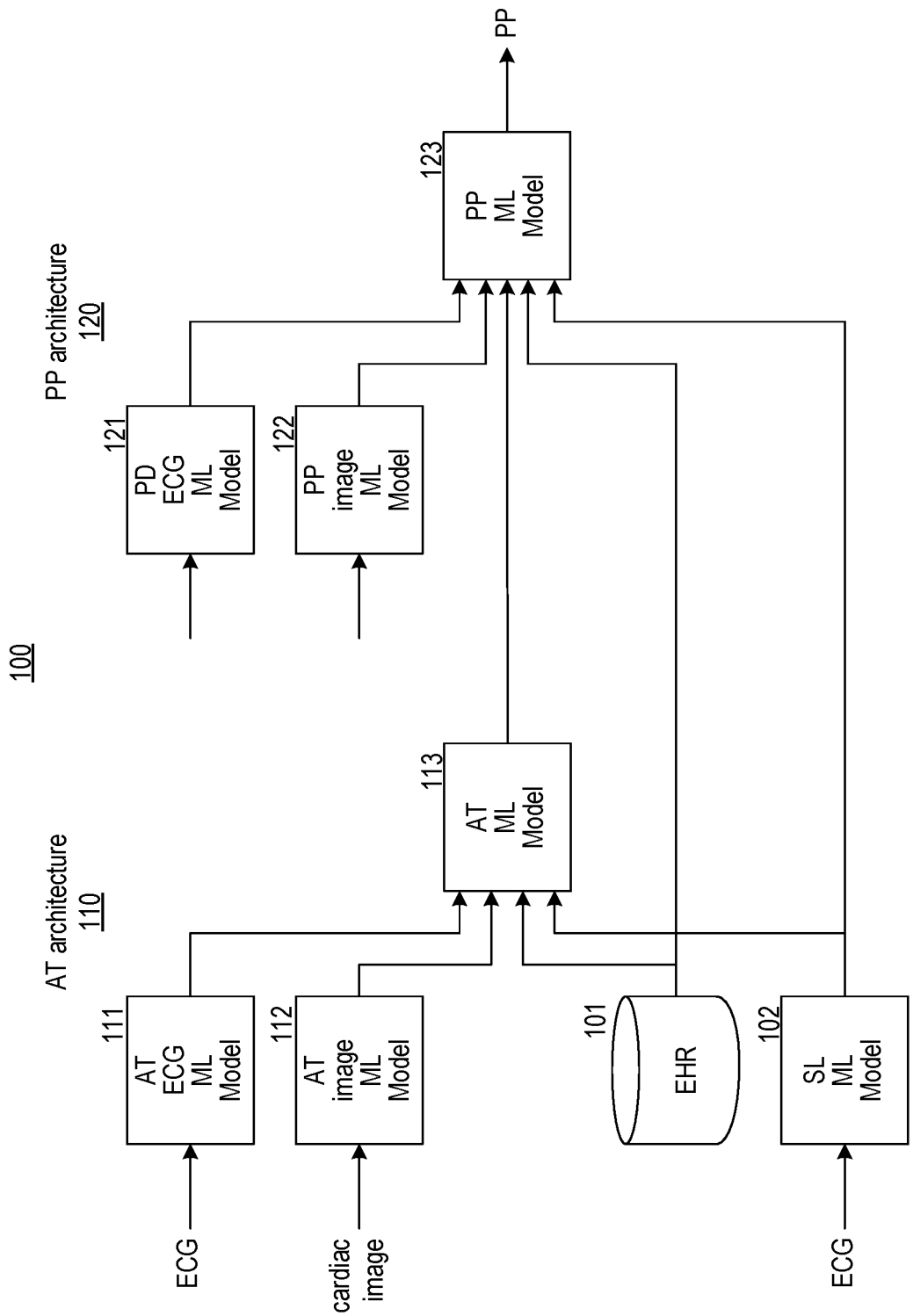
FIG. 1 is a block diagram that illustrates an example TP architecture.

Methods and systems are provided to support an ablation procedure by providing an ablation target (AT) and a tunable parameter plan (PP) for the ablation procedure. In some embodiments, a targeting and planning (TP) system provides an AT system that generates an AT and a PP system that generates a PP. An AT defines a target region that is the target of the ablation and that may be distal from the source location of the arrhythmia (e.g., does not include the source location). An AT may be specified by a start location and an end location of a line, a sequence of locations, a curved line, or more generally an ablation pattern. A PP may be specified by device characteristics and parameter values for tunable parameters of an ablation device.

The AT system may be implemented using machine learning (ML). To identify an AT for a patient, the AT system inputs a patient data set into an AT ML model which outputs the AT. A patient data set may include a patient electrogram, a patient cardiac image (e.g., CT image or MRI image), patient health data (e.g., prior ablation information), and so on. The AT system may train an AT ML model using simulated data and/or clinical data to identify an AT. The simulated data comprises simulated data sets that may include a simulated cardiogram, a simulated cardiac image, simulated health data, and a simulated AT. A clinical data set may include a clinical cardiogram, a clinical cardiac image, clinical health data, and a clinical AT of an electronic health record (EHR) of a person. A simulated or clinical AT of a data set is an AT that is considered effective given that data set.

To train the AT ML model, the AT system uses training data that includes training data sets with a feature vector and a label. A feature vector has features that may include a training cardiogram, a training cardiac image, and training health data. A label represents a training AT. The training AT of a training data set represents an AT that may be appropriate for a patient with a patient feature vector that matches the training feature vector of that training data set. The training AT may be a location other than the source location. After the AT ML model is trained, the AT system applies the AT ML model to a patient feature vector that comprises patient features representing a patient cardiogram, a patient cardiac image, and a patient health data to generate a patient AT. The AT system outputs the patient AT to help inform an ablation procedure for the patient. The patient AT may be output by displaying on a computer display, sending to an ablation device, sending to cardiac mapping system, storing in the patient health record of the patient, and so on.

The PP system may also be implemented using ML. To create a PP for a patient, the PP system applies a PP ML model to a patient data set for the patient. The patient data set may include a patient cardiogram, a cardiac image, and other patient health data. The PP system trains the PP ML model using clinical data sets that include a clinical cardiogram and a clinical PP of an EHR of a person. The clinical PP may represent the actual PP that was deemed successful (e.g., by an electrophysiologist) in treating that person. The success may also be inferred based on analysis of the EHR. For example, if a patient has an ablation but does not have any subsequent arrhythmia detected for some number of years, the PP (or AT) may be deemed to be successful.

To train the PP ML model, the PP system uses training data that includes training data sets with a feature vector and a label. A feature vector has features that may include a training cardiogram, training health data, and a label that represents a training PP. After the PP ML model is trained, the PP system applies the PP ML model to a patient feature vector that comprise patient features representing a patient cardiogram and patient health data to generate a patient PP. The PP system outputs the patient PP to help inform an ablation procedure for the patient. The patient PP may be output by displaying on a computer display, sending to an ablation device, sending to cardiac mapping system, storing in the patient health record of the patient, and so on.

In some embodiments, the PP system may also train a PP ML model based on simulations of lesion development in cardiac tissue. The training data used to train such a PP ML model may be training features derived from clinical data sets labeled with PPs resulting in lesions that are considered effective at treating an arrhythmia. Techniques for simulating lesion development based on a PP (also referred to as a delivery plan) are described in U.S. Pro. App. No. 63/627,047 entitled "Delivery Plan Evaluation System" and filed on Jan. 30, 2024, which is hereby incorporated by reference.

The TP system may employ various ML architectures for the AT ML model and the PP ML model. FIG. 1 is a block diagram that illustrates an example TP architecture. The TP architecture 100 includes an AT architecture 110 and a PP architecture 120. The AT architecture 110 includes an AT ECG ML model 111, an AT image ML model 112, and an AT ML model 113. The AT ECG ML model inputs an ECG and outputs a representation of the ECG. The AT ECG ML model may be based on an autoencoder with the latent vectors being the representations. An ECG may be represented in various formats such as an image (e.g., pixel values) or voltage-time series. The representation of the ECG may alternatively be based on measurements derived from the ECG such as R-R interval, maximum voltage, QRS integral, and so on. An ECG image or ECG voltage-time series may be used as the representation without or in addition to generating another representation. The AT image ML model inputs a cardiac image (e.g., of the thorax) and outputs a representation of heart within the cardiac image. The AT ML model inputs a feature vector with features including the representations of the ECG and the cardiac image, health data of an EHR data store 101, and a source location of an arrhythmia which may be generated by a source location (SL) ML model 102. The AT ECG ML model may be, for example, a convolutional neural network (CNN), an autoencoder, a transformer (or another attention-based model), a recurrent neural network, and so on that output the ECG representation or encoding. The AT image ML model may include a CNN for each slice of the cardiac image (e.g., a CT image) that inputs a slice and outputs a slice encoding and may include a neural network (NN) that inputs the slice encodings and outputs a three-dimensional (3D) mesh representing the cardiac geometry represented by the cardiac image. The AT image model may also be a 3D CNN. Additional techniques for generating a 3D mesh are described in PCT Pub. No. US2022/14406 entitled "Overall Ablation Workflow System" and filed on Mar. 3, 2023, which is hereby incorporated by reference. The SL ML model may be the ML as described in the '816 patent. The AT ML model may be an NN that inputs the ECG encoding, the 3D mesh, health data, and the source location and outputs the AT. The AT ECG ML model, the AT image ML model, and the AT ML model may be trained separately or may be trained together with a combined loss function. Rather than using NNs, the AT ML model may be based on a recommender system, a K-Nearest Neighbor system architecture, and so on as described below. Although the TP system is described primarily as using an electrogram that is an ECG, the TP system may use other types of electrograms. Electrograms include tissue electrograms and cardiograms. Tissue electrograms include endocardial electrograms collected while an electrode is contact with the endocardium and epicardial electrograms collected while an electrode is in contact with the epicardium. Cardiograms include ECGs and VCGs. More generally, an electrogram is any measure of electrical activity of a heart.

The PP architecture includes a PP ECG ML model 121, a PP image ML model 122, and a PP ML model 123. The PP ECG ML model inputs an ECG, and the PP image ML model inputs a cardiac image. These ML models may be the same as the AT ECG ML model and the AT image ML model, respectively. In such a case, the output of the AT ECG ML model and the AT image ML model may be input directly to the PP ML model. The PP ML model inputs a representation of an ECG and a cardiac image, health data, and an AT or SL or both and outputs a PP. The PP ML model may be an NN, a recommender system, a K-Nearest Neighbor system, and so on as described above for the AT ML model.

The AT ML model and the PP ML model may also be used independently. In such a case, the AT and/or source location may not be available to the PP ML model. If not available, the AT and/or the SL may be inferred as a hidden feature from output of the PP ECG ML model and the PP image ML model. Alternatively, the SL may be a simulated SL used in a simulation or a clinical SL of an EHR.

The TP system may also employ additional features. For example, one feature may be the arrhythmia type such as AF and AFL and for AFL the flutter type such as typical or atypical. Another feature may be the cardiac chamber in which the arrhythmia is thought to originate. For training data, this feature may be determined from simulated data or clinical data. When applying the AT ML model or the PP ML model, a medical provider may specify the cardiac chamber that the arrhythmia is thought to originate. Rather than using arrhythmia type, flutter type, or cardiac chamber as features, the TP system may employ separate ML models for various combinations of these features. For example, an AF AT ML model may be trained using simulated data or clinical data representing a person with AF, and an AFL/atypical AT ML model may be trained using clinical data representing a person with an AFL that is atypical.

In some embodiments, the AT system may run simulations to support identifying an AT. The simulations may be used to generate training data for the ML models of the AT system or to identify an AT without using an ML model. The AT system employs computational modeling to simulate the electromagnetic (EM) output of a heart over time based on a source configuration of the heart. The EM output may represent an electrical voltage, a current, a magnetic field, and so on. The source configuration may include information on cardiac geometry, cardiac muscle fibers, scar locations, a source location of an arrhythmia, electrical properties (e.g., action potential and conduction velocity), and so on, and the EM output is a collection of the electrical characteristics (e.g., voltages) at various heart locations within the myocardium over time. The source configurations may be derived from simulated data, clinical data, or patient-specific data. To generate the EM output, a simulation may be performed with simulation steps at step intervals (e.g., 1 ms) to generate an EM mesh for that step. The EM mesh may be a finite-element three-dimensional (3D) mesh that stores an EM value (e.g., voltage) at each heart location (i.e., vertex of the mesh) for that step. For example, the left ventricle may be defined as having approximately 70,000 heart locations with the EM mesh storing an EM value for each heart location. With such an EM mesh, a three-second simulation with a step interval of 1 ms would generate 3,000 sets of 70,000 EM values. The sets of EM values are the EM output of the simulation. Computational modeling is described in Villongco, C., Krummen, D., et al., "Patient-Specific Modeling of Ventricular Activation Pattern using Surface ECG-derived Vectorcardiogram in Bundle Branch Block," Progress in Biophysics and Molecular Biology, vol. 115, iss. 2-3, August 2014, pp. 305-313. The AT system also generates an ECG or other cardiogram for each simulation based on the EM outputs of the simulation steps assuming various thoracic characteristics (e.g., body fat composition).

To generate training data, the AT system accesses training cardiac images, training health data, and training source configuration data (e.g., source location). For each cardiac image, the AT system generates a 3D mesh based on the cardiac geometry represented by the cardiac image. The AT system initializes data of each vertex, for example, to represent normal tissue, scar tissue, a reentrant circuit, an ablation pattern, a PVI, and so on. The AT system may run multiple simulations, each starting with that initialized data but with different source locations. If a simulation results in inducing a simulated arrhythmia, the AT system generates an ECG based on the EM output of the simulation. The AT system then continues that simulation multiple times each assuming a different AT. The AT system adds an ablation (e.g., scar tissue characteristics) at the AT to the 3D mesh to simulate an ablation and continues the simulation from the point at which the simulated arrhythmia was induced. If the simulated arrhythmia is terminated based on the added AT, the AT system indicates that that AT is effective for a person with an arrhythmia ECG, a cardiac image, health data, and source configuration data that is similar to that of the simulation. If multiple ATs are effective, the AT system may generate a score for each as discussed below. The AT system generates a training data set for each simulation for which the arrhythmia was terminated. The simulations including the patient-specific simulations may be bootstrapped using techniques as described in the '816 patent. Techniques for evaluating the effectiveness of ATs (e.g., ablation patterns) are described in U.S. Pat. No. 11,259,871 entitled "Identify Ablation Pattern for Use in an Ablation" and issued on Mar. 1, 2022, which is hereby incorporated by reference.

The AT system may perform patient-specific simulations in an analogous manner but based on a cardiac image of the patient's heart and health data (e.g., scar tissue, prior ablations) of the patient. The AT system runs the simulations assuming an SL such as one identified by an SL ML model. If a simulated arrhythmia is induced, the AT system then, for each possible AT (or combinations of ATs), continues the simulation assuming that AT. If an AT is successful at terminating the arrhythmia, the AT is designated as being effective. If multiple ATs are effective, the AT system may output those ATs and may generate an AT score based on location of the AT (e.g., near a nerve) to assist a medical provider in selecting which effective AT to use. The AT system may also run multiple simulations with different source locations. Each simulation is run until an arrhythmia is induced and a simulated ECG is generated. The AT system then compares a patient arrhythmia ECG to the simulated ECGs and selects a simulated ECG that matches (based on a similarity criterion such as cross-correlation, Pearson similarity, and cosine similarity) the patient arrhythmia ECG. The AT system then continues that simulation of that matching simulated ECG for different ATs to determine if the ATs are effective at terminating the arrhythmia based on the simulated SL. If the simulated ECG that is most similar to the patient arrhythmia ECG does not satisfy the similarity criterion, the AT system may run additional simulations until an arrhythmia is induced. Each simulation assumes a simulated SL that is near the simulated SL associated with the most similar simulated ECG. If a simulated ECG generated from such a simulation matches the patient arrhythmia ECG, the AT system runs multiple continuation simulations with different ATs to identify an AT that terminates the arrhythmia.

Figure 2:
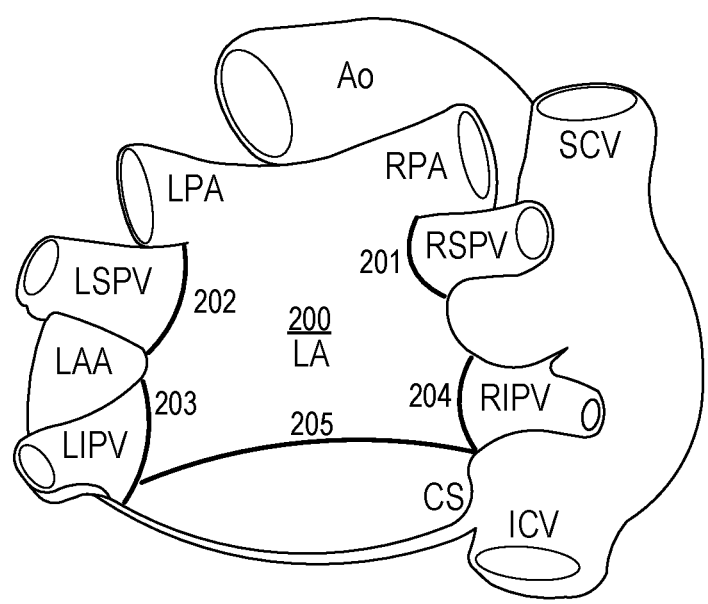
FIG. 2 is a diagram that illustrates lines of a PVI.

FIG. 2 is a diagram that illustrates lines of a PVI. The left atrium (LA) is shown with four ablation lines: ablation line 201 for the right superior pulmonary vein (RSPV), ablation line 202 for the left superior pulmonary vein (LSPV), ablation line 203 for the left inferior pulmonary vein (LIPV), and ablation line 204 for the right inferior pulmonary vein (RIPV). Ablation line 205 represents an AT identified by the AT system after the PVI was performed. The AT system may be used to identify an AT during an ablation procedure. In this example, the AT system may be employed during a PVI procedure. After the PVI is performed, the patient may be paced in an attempt to induce an arrhythmia. If an arrhythmia is induced, the AT system may be used to identify an AT such as ablation line 205. The PP system may similarly be used during a procedure to identify a PP for an ablation. Although the TP system is described primarily in the context of using an ECG to identify an AT and PP, other cardiograms may be used. For example, electrogram may be the electrical signal collected by a pacing catheter, by a vectorcardiogram (VCG) generated from an ECG, and so on. During a procedure, the TP system may input an electrogram collected from a pacing catheter. The TP system may employ separate ML models for each type of cardiogram.

Figure 3:
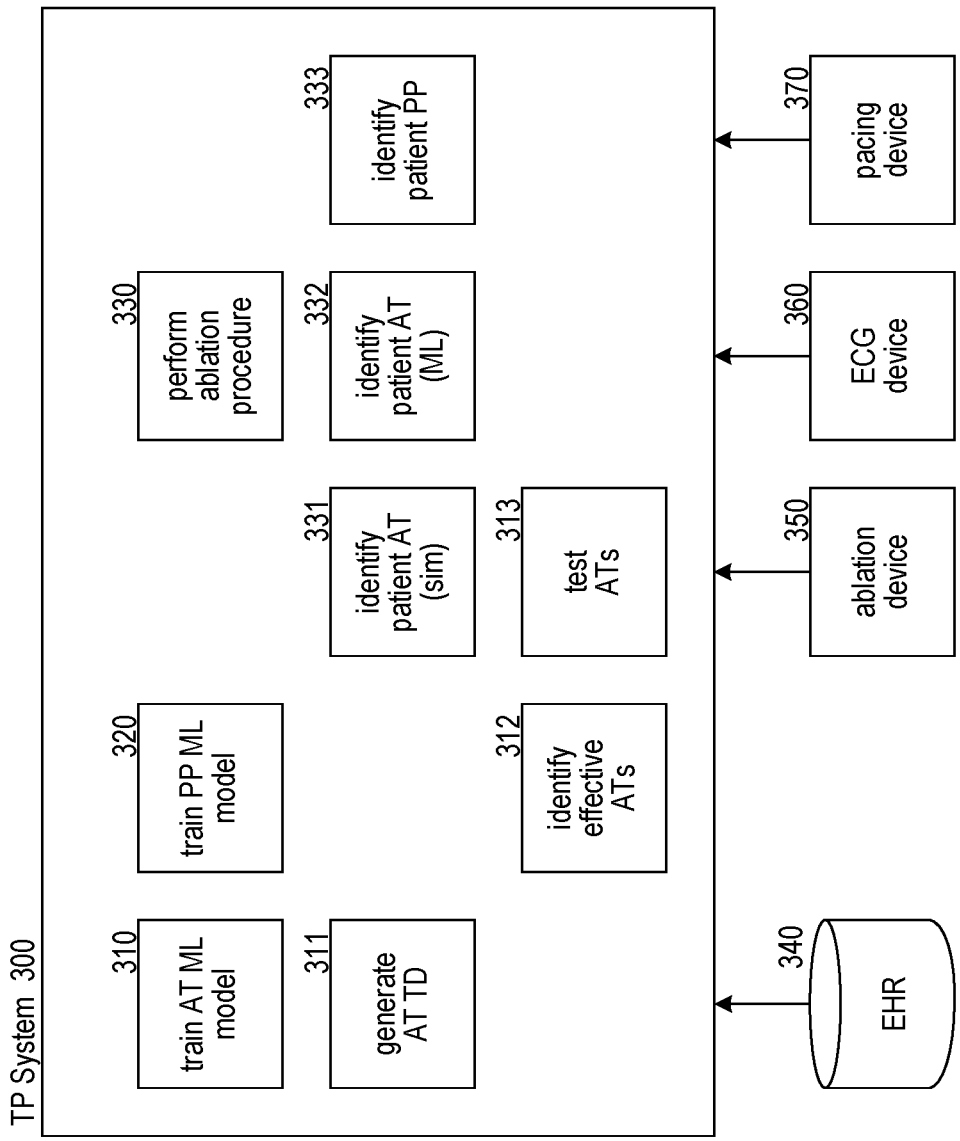
FIG. 3 is a block diagram that illustrates components of the TP system in some embodiments.

FIG. 3 is a block diagram that illustrates components of the TP system in some embodiments. The TP system 300 includes a train AT ML model component 310, a train PP ML model component 320, and a perform ablation procedure component 330. The train AT ML model component generates training data that may be simulated or clinical and then trains the AT ML model. A generate AT training data component 311 generates simulated training data and invokes an identify effective ATs component 312. The identify effective ATs component runs simulations and invokes a test ATs component 313 to determine which ATs are effective at terminating a simulated arrhythmia. The train PP ML component is invoked to train the PP ML model. The perform ablation procedure component is invoked to support an ablation procedure. The perform ablation procedure component may invoke an identify patient AT (sim) component 331 to identify an AT using simulations, an identify patient AT (ML) component 332 to identify an AT using ML, and an identify patient PP component 333 to identify a patient PP for a patient. The TP system interfaces with an EHR system 340, an ablation device 350, an ECG device 360, and a pacing device 370 and may also interface with an imaging device.

The computing systems (e.g., network nodes or collections of network nodes) on which the TP system and the other described systems may be implemented may include a central processing unit, input devices, output devices (e.g., display devices and speakers), storage devices (e.g., memory and disk drives), network interfaces, graphics processing units, communications links (e.g., Ethernet, Wi-Fi, cellular, and Bluetooth), global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, distributed systems, cloud-based computing systems, client computing systems that interact with cloud-based computing system, desktop computers, laptops, tablets, e-readers, personal digital assistants, smartphones, gaming devices, servers, and so on. The computing systems may access computer-readable media that include computer-readable storage mediums and data transmission mediums. The computer-readable storage mediums are tangible storage means that do not include a transitory, propagating signal. Examples of computer-readable storage mediums include memory such as primary memory, cache memory, and secondary memory (e.g., DVD), and other storage. The computer-readable storage media may have recorded on them or may be encoded with computer-executable instructions or logic that implements the TP system and the other described systems. The data transmission media are used for transmitting data via transitory, propagating signals or carrier waves (e.g., electromagnetism) via a wired or wireless connection. The computing systems may include a secure crypto processor as part of a central processing unit (e.g., Intel Secure Guard Extension (SGX)) for generating and securely storing keys and for encrypting and decrypting data using the keys and for securely executing all or some of the computer-executable instructions of the TP system. Some of the data sent by and received by the TP system may be encrypted, for example, to preserve patient privacy (e.g., to comply with government regulations such the European General Data Protection Regulation (GDPR) or the Health Insurance Portability and Accountability Act (HIPAA) of the United States). The TP system may employ asymmetric encryption (e.g., using private and public keys of the Rivest-Shamir-Adleman (RSA) standard) or symmetric encryption (e.g., using a symmetric key of the Advanced Encryption Standard (AES)).

The one or more computing systems may include client-side computing systems and cloud-based computing systems (e.g., public or private) that each executes computer-executable instructions of the TP system. A client-side computing system may send data to and receive data from one or more servers of the cloud-based computing systems of one or more cloud data centers. For example, a client-side computing system may send a request to a cloud-based computing system to perform tasks such as run a patient-specific simulation of electrical activity of a heart or train a patient-specific ML model. A cloud-based computing system may respond to the request by sending to the client-side computing system data derived from performing the task such as an SL of an arrhythmia. The servers may perform computationally expensive tasks in advance of processing by a client-side computing system such as training a ML model or in response to data received from a client-side computing system. A client-side computing system may provide a user experience (e.g., user interface) to a user of the TP system. The user experience may originate from a client computing device or a server computing device. For example, a client computing device may generate a patient-specific graphic of a heart and display the graphic. Alternatively, a cloud-based computing system may generate the graphic (e.g., in a Hyper-Text Markup Language (HTML) format or an extensible Markup Language (XML) format) and provide it to the client-side computing system for display. A client-side computing system may also send data to and receive data from various medical devices such as an ECG monitor, an ablation therapy device, an ablation planning device, and so on. The data received from the medical devices may include an ECG, actual ablation characteristics (e.g., ablation location and ablation pattern), and so on. The data sent to a medical device may include data, for example, data in a Digital Imaging and Communications in Medicine (DICOM) format. A client-side computing device may also send data to and receive data from medical computing systems. Such medical computing systems store patient medical history data, descriptions of medical devices (e.g., type, manufacturer, and model number) of a medical facility, medical facility device descriptions, results of procedures, and so on. The term cloud-based computing system may encompass computing systems of a public cloud data center provided by a cloud provider (e.g., Azure provided by Microsoft Corporation) or computing systems of a private server farm (e.g., operated by the provider of the TP system).

The TP system and the other described systems may be described in the general context of computer-executable instructions, such as program modules and components, executed by one or more computers, processors, or other devices. Generally, program modules or components include routines, programs, objects, data structures, and so on that perform tasks or implement data types of the TP system and the other described systems. Typically, the functionality of the program modules may be combined or distributed as desired in various examples. Aspects of the TP system and the other described systems may be implemented in hardware using, for example, an application-specific integrated circuit (ASIC) or a field programmable gate array (FPGA).

Figure 4:
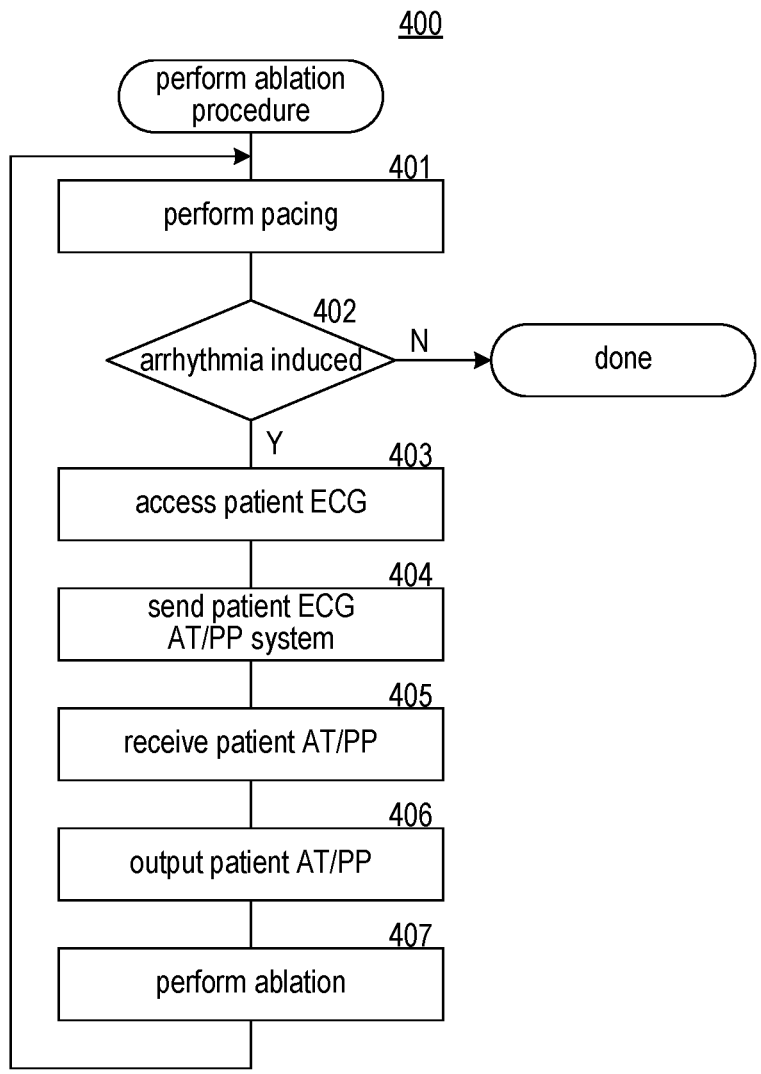
FIG. 4 is a flow diagram that illustrates the processing of a perform ablation procedure component in some embodiments.

FIG. 4 is a flow diagram that illustrates the processing of a perform ablation procedure component in some embodiments. The perform ablation procedure component 400 coordinates the performing of pacing, identifying of an AT and PP, and directing an ablation to be performed. In block 401, the component directs the performing of pacing. In decision block 402, if the pacing induces an arrhythmia, then the component continues at block 403, else the component completes. A medical provider may indicate that an arrhythmia is induced. Alternatively, automatic techniques may be employed to determine if an arrhythmia is induced such as those described in U.S. App. No. 63/401,106 entitled "Automatic Fibrillation Classification and Identification of Fibrillation Epochs" and filed on Aug. 25, 2022, which is hereby incorporated by reference. In block 403, the component accesses a patient arrhythmia ECG. In block 404, the component sends the patient arrhythmia ECG to the TP system. In block 405, the component receives the patient AT and patient PP from the TP system. In block 406, the component outputs the patient AT and patient PP, for example, by displaying or sending to an ablation planning device. In block 407, the component directs performing of the ablation and loops to block 401 to direct that pacing be performed in an attempt to induce an arrhythmia after the ablation is performed. If a medical provider indicates that another ablation may be performed (e.g., because an arrhythmia was induced), the component updates the patient data based on the last ablation. The patient data may be updated to include, for example, an ablation pattern and lesion characteristics of the last ablation. The ablation pattern may be determined based on tracking movement of a catheter (or other ablation device (e.g., an external radiation source) when ablating tissue. The lesion characteristics may be determined by simulating lesion developments, for example, as described in the '047 provisional application. The ablation pattern and lesion characteristics may also be identified based on analysis of images collected during the procedure. The component then performs the processing of blocks 403-407.

Figure 5:
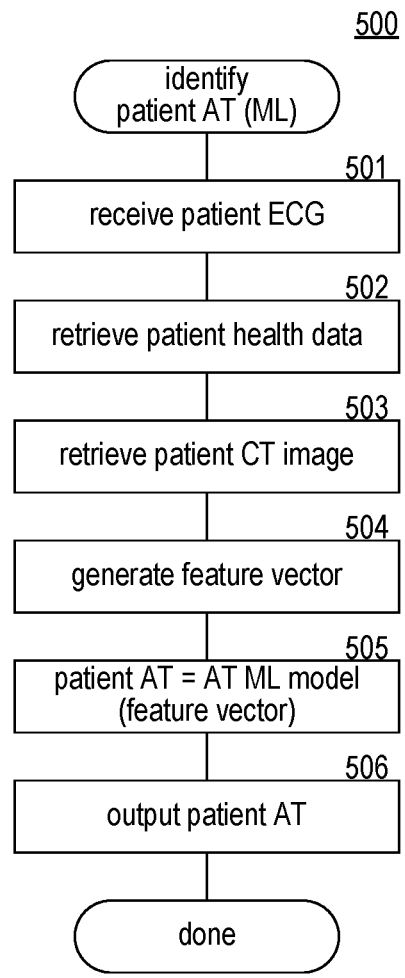
FIG. 5 is a flow diagram that illustrates the processing of an identify patient AT (ML) component in some embodiments.

FIG. 5 is a flow diagram that illustrates the processing of an identify patient AT (ML) component in some embodiments. The identify patient AT (ML) component 500 is invoked prior to and/or during a procedure to determine an AT for a patient using ML. In block 501, the component receives the patient arrhythmia ECG from an EHR or an ECG device. In block 502, the component retrieves patient health data from the EHR of the patient. In block 503, the component retrieves a patient CT image from the EHR of the patient. In block 504 the component generates a feature vector based on the patient ECG, the patient CT image, and the patient health data (e.g., prior ablation location, scar tissue location). In block 505, the component applies the AT ML model to the feature vector to generate a patient AT. In block 506, the component outputs the patient AT, for example, to a display or to an ablation device that controls the overall processing of an ablation. Techniques for generating a delivery plan are described in PCT Pub. No. US2022/14406. The component then completes.

Figure 6:
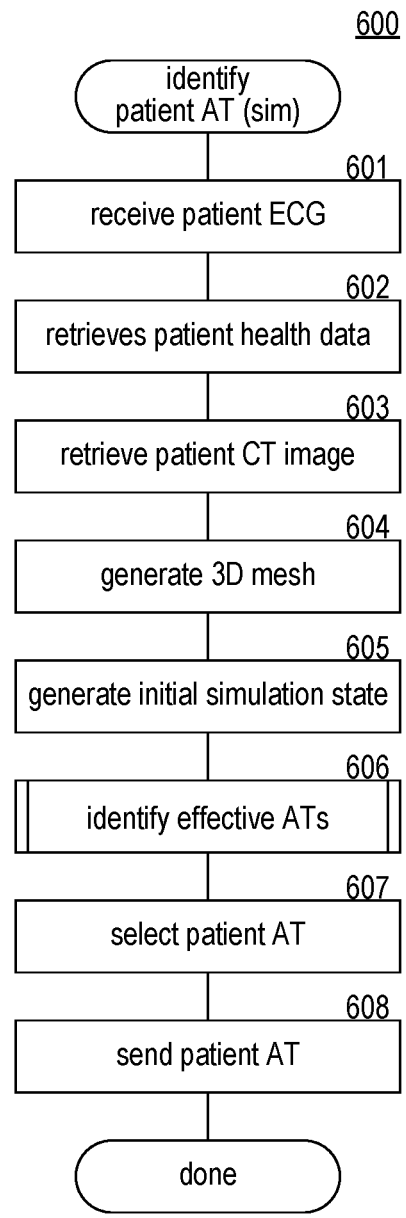
FIG. 6 is a flow diagram that illustrates the processing of an identify patient AT (sim) component in some embodiments.

FIG. 6 is a flow diagram that illustrates the processing of an identify patient AT (sim) component in some embodiments. The identify patient AT (sim) component 600 is invoked to identify a patient AT using simulations. In block 601, the component retrieves a patient ECG. In block 602, the component retrieves patient health data from the EHR of the patient. In block 603, the component retrieves a patient CT image from the electronic health record. In block 604, the component generates a 3D mesh based on the CT image. Techniques for generating a 3D mesh are described in PCT Pub. No. US2022/14406. In block 606, the component generates an initial simulation state. In block 606, the component invokes an identify effective ATs component to determine which ATs would be effective in treating the patient based on running simulations. In block 607, the component selects one or more patient ATs from the collection identified effective ATs. In block 608, the component then outputs the selected patient ATs to, for example, a display device or an ablation device that coordinates the performing of the ablation. The component then completes.

Figure 7:
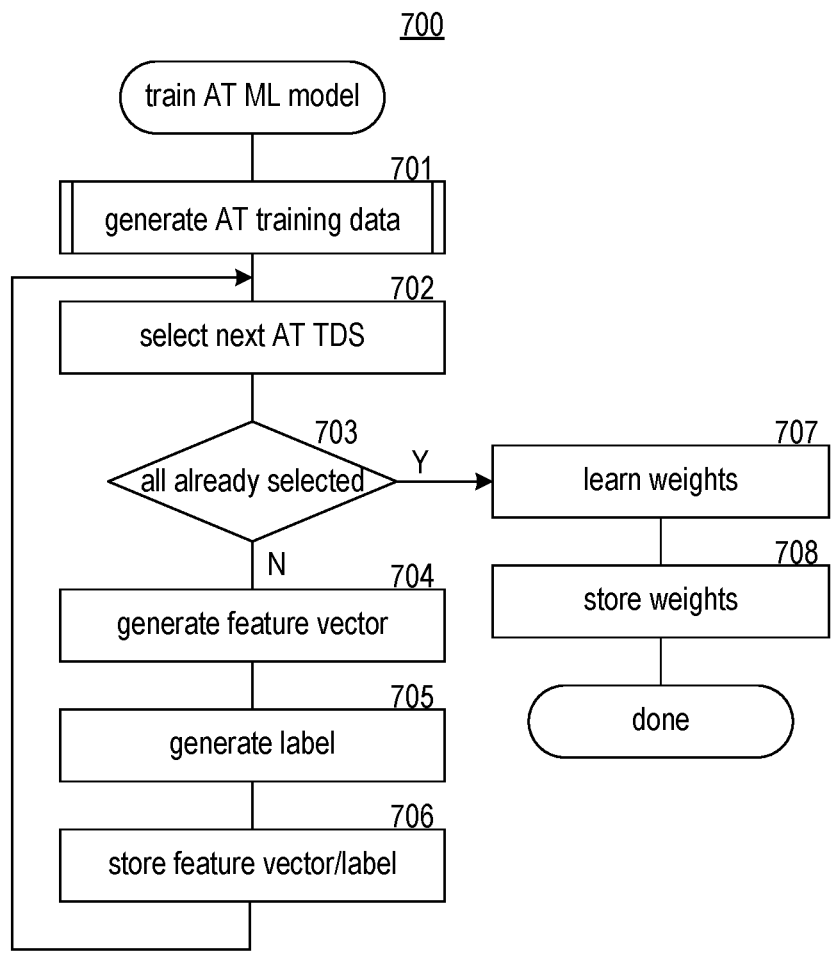
FIG. 7 is a flow diagram that illustrates the processing of a train AT ML model in some embodiment.

FIG. 7 is a flow diagram that illustrates the processing of a train AT ML model in some embodiment. The train AT ML model 700 is invoked to train an AT ML model. In block 701, the component invokes a generate AT training data component to generate the training data for training the AT ML model. In block 702, the component selects the next AT training data set of the AT training data. In decision block 703, if all the AT training data sets have already been selected, then the component continues at block 707, else the component continues at block 704. In block 704, the component generates a feature vector based on features of the training data set. In block 705, the component generates a label based on the AT of the training data set. In block 706, the component stores the feature vector and the label and then loops to block 702 to select the next AT training data set. In block 707, the component trains the model using the stored feature vectors and labels to learn the weights. In block 708, the component stores the weights and then completes.

Figure 8:
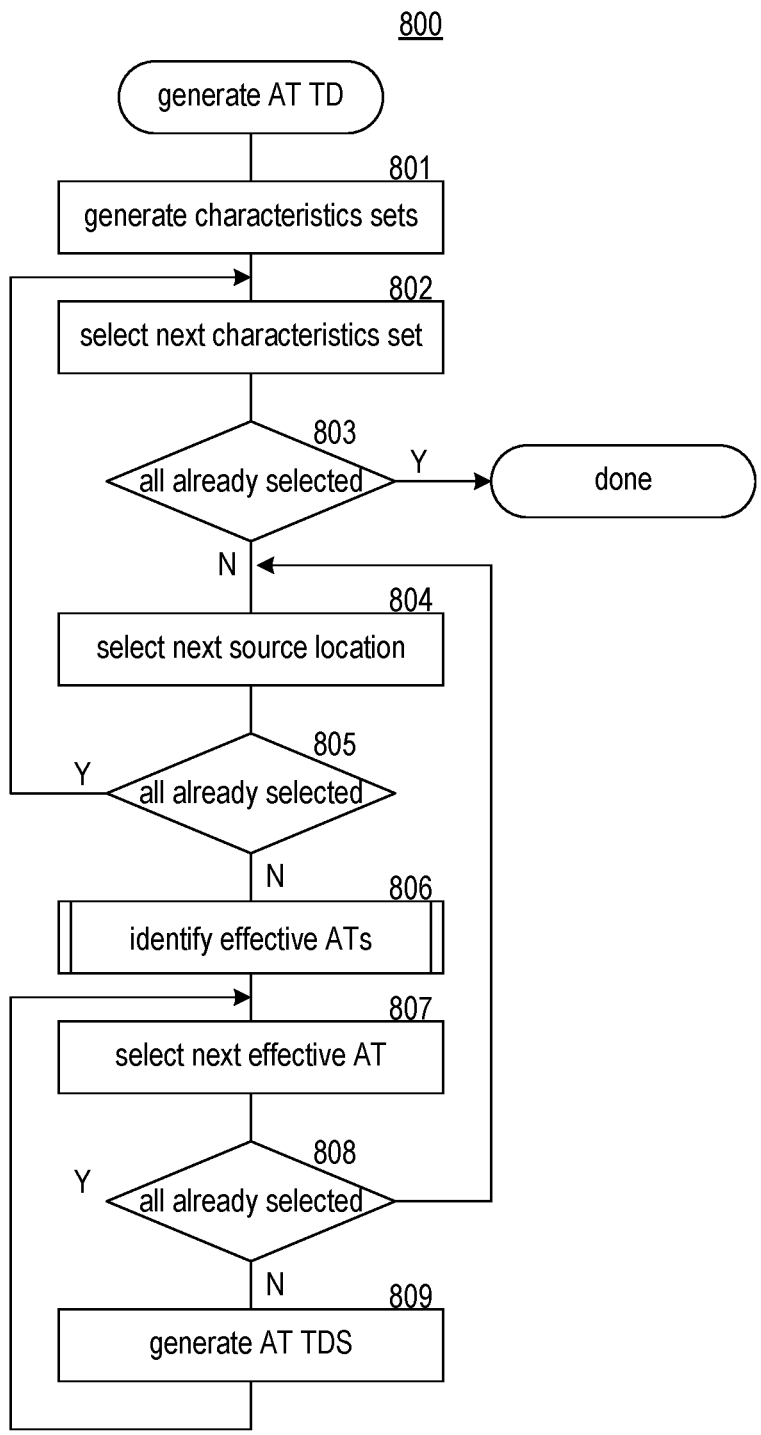
FIG. 8 is a flow diagram that illustrates the processing of a generate AT training data component in some embodiments.

FIG. 8 is a flow diagram that illustrates the processing of a generate AT training data component in some embodiments. The generate AT training data component 800 generates AT training data having training data sets for training the AT ML model. In block 801, the component generates training characteristics sets that include an ECG, a CT image, and health data. The characteristic sets may be generated based on simulated and/or clinical data. In block 802, the component selects the next characteristics set. In decision block 803, if all the characteristic sets have already been selected, then the component completes, else the component continues at block 804. In block 804, the component selects another source location. In decision block 805, if all the source locations have already been selected, then the component loops to block 802 to select the next characteristics set, else the component continues at block 806. In block 806, the component invokes an identify effective ATs component to identify ATs that are effective for treating arrhythmia that originates at that source location. In block 807, the component selects the next effective AT. In decision block 808, if all the effective ATs have already been selected, then the component loops to block 804 to select the next source location, else the component continues at block 809. In block 809, the component generates an AT training data set based on the effective AT and then loops to block 807 to select the next effective AT.

Figure 9:
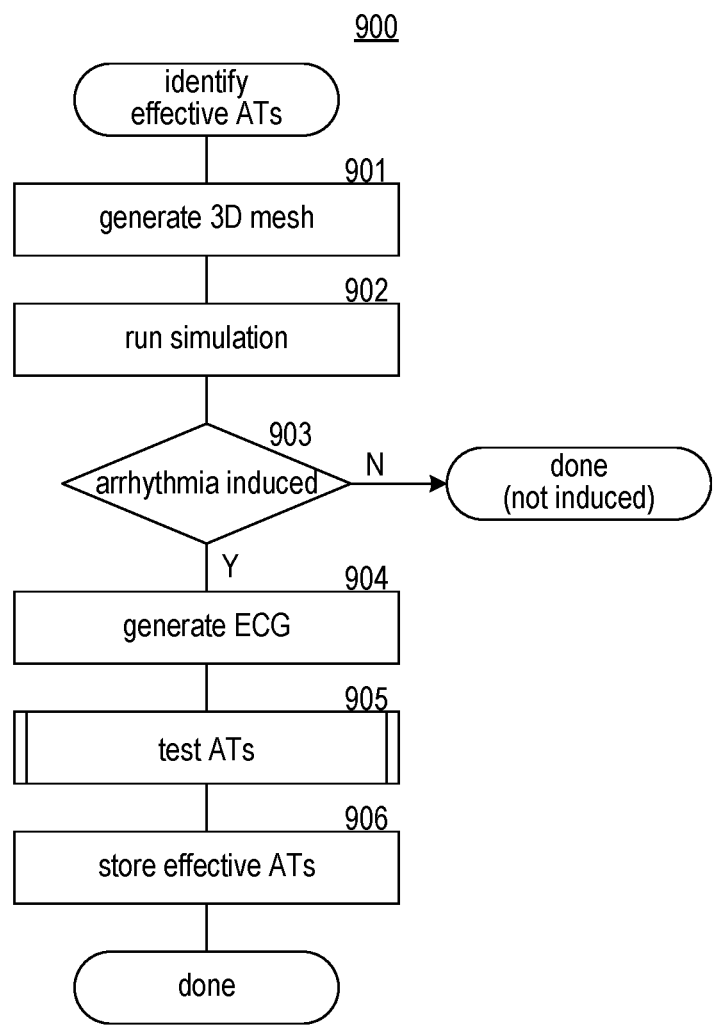
FIG. 9 is a flow diagram that illustrates the processing of an identify effective ATs component in some embodiments.

FIG. 9 is a flow diagram that illustrates the processing of an identify effective ATs component in some embodiments. The identify effective ATs component is provided a characteristics set and an SL and determines whether that source location is effective at terminating an arrhythmia that originates at that source location given that characteristics set. In block 901, the component generates a 3D mesh based on the CT image of the characteristics set. In block 902, the component runs a simulation using that 3D mesh, data of the characteristics set (e.g., scar location), and the source location. In decision block 903, if the simulation induces an arrhythmia, then the component continues at block 904, else the component completes indicating that an arrhythmia was not induced. In block 904, the component generates an ECG based on EM output of the simulation and stores the ECG. In block 905, the component invokes a test ATs component to test which ATs are effective at terminating the arrhythmia. In block 906, the component stores the effective ATs and then completes.

Figure 10:
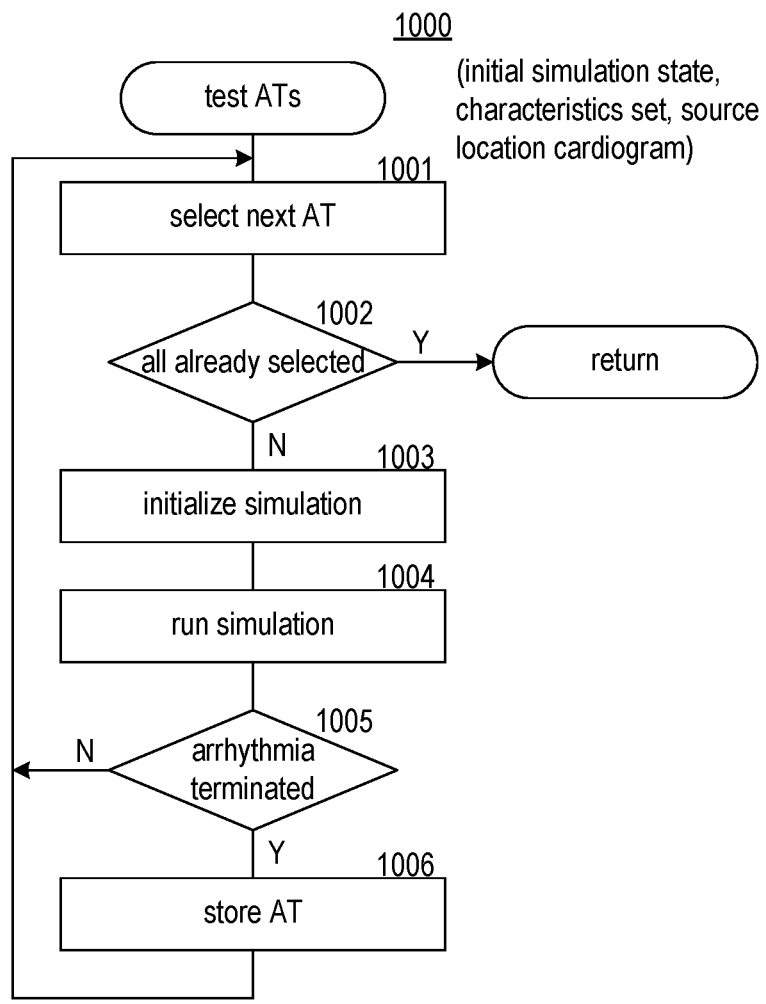
FIG. 10 is a flow diagram that illustrates the processing of a test ATs component in some embodiments.

FIG. 10 is a flow diagram that illustrates the processing of a test ATs component in some embodiments. The test ATs component 1000 is invoked to identify ATs are effective at terminating an arrhythmia. In block 1001, the component selects a possible AT. In decision block 1002, if all the ATs have already been selected, then the component returns, else the component continues at block 1003. In block 1003, the component initializes a simulation based on the state of the simulation when the arrhythmia was induced and with an indication of an ablation based on the AT. In block 1004, the component then runs the simulation. The simulation may also be considered to be a continuation of the simulation that induces the arrhythmia. In decision block 1005, if the arrhythmia is terminated, then the component continues at block 1006, else the component loops to block 1001 to select the next AT. In block 1006, the component stores the AT as an effective AT and then loops to block 1001 to select the next AT.

Figure 11:
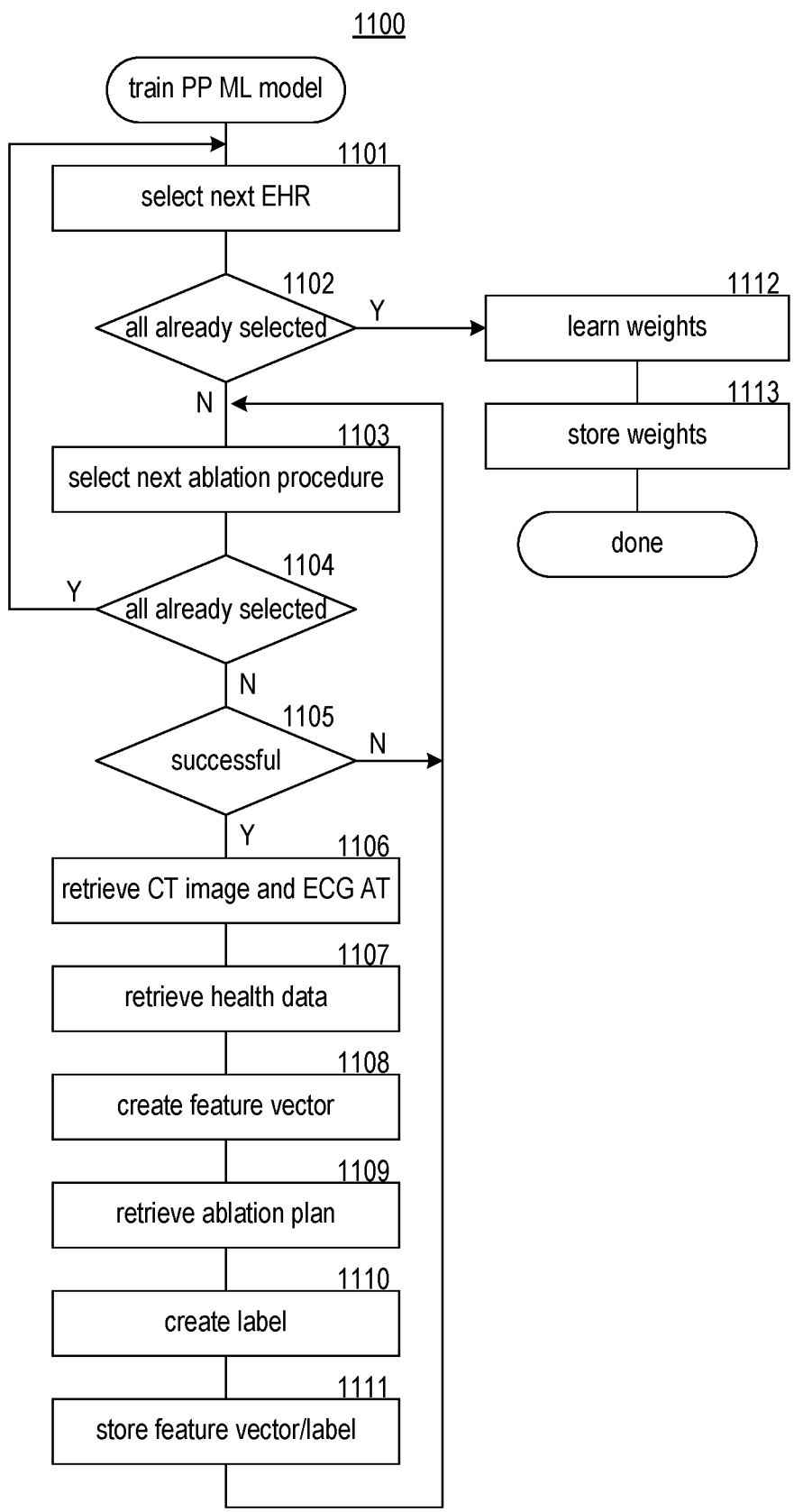
FIG. 11 is a flow diagram that illustrates the processing of a train PP ML model in some embodiments.

FIG. 11 is a flow diagram that illustrates the processing of a train PP ML model in some embodiments. The train PP ML model 1100 is invoked to train a PP ML model using clinical data of EHRs. In block 1101, the component selects the next EHR. In decision block 1102, if all the EHRs have already been selected, then the component continues at block 1112, else the component continues at block 1103. In block 1103, the component selects the next ablation procedure of that EHR. In decision block 1104, if all the ablation procedures have already been selected, then the component loops to block 1101 to select the next EHR, else the component continues at block 1105. In decision block 1105, if the ablation procedure was successful, then the component continues at block 1106, else the component loops to block 1103 to select the next ablation procedure. An ablation may be determined to be successful based on an ablation success criterion based on comments in the EHRs, time since the ablation procedure with no subsequent ablation procedures, and so on. In block 1106, the component retrieves an arrhythmia ECG, CT image, a source location, and the ablation location from the EHR. The source location may alternatively be identified by applying a mapping system to the ECG. In block 1107, the component retrieves other health data from the EHR. In block 1108, the component creates a feature vector based on the retrieved data. In block 1109, the component retrieves an ablation plan from the EHR. In block 1110, the component creates a label based on the ablation plan. In block 1111, the component stores the feature vector and label as training data and then loops to block 1103 to select the next ablation procedure. In block 1112, the component trains the ML model using the training data to learn the weights. In block 1113, the component stores the weights and then completes.

Figure 12:
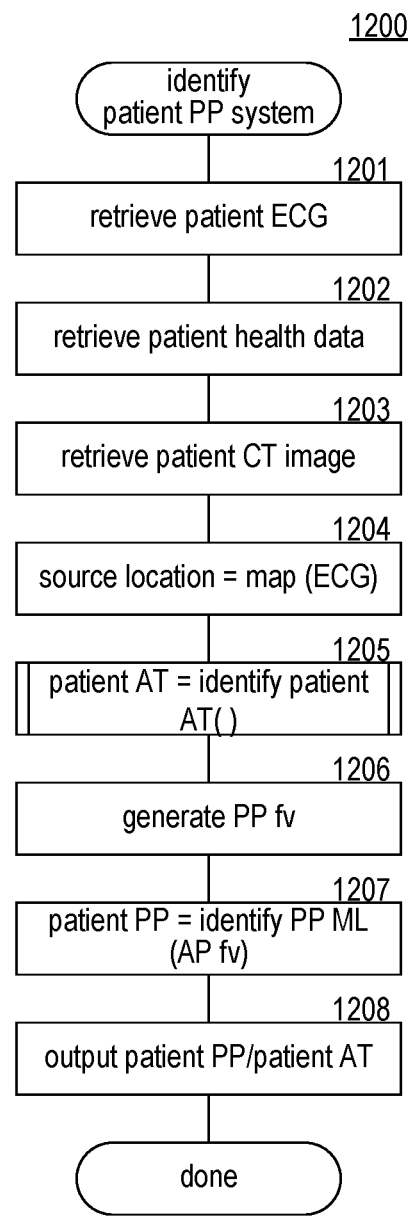
FIG. 12 is a flow diagram that illustrates the processing of an identify patient PP system in some embodiments.

FIG. 12 is a flow diagram that illustrates the processing of an identify patient PP system in some embodiments. The identify patient PP system 1200 is invoked to identify a patient PP given an EHR. In block 1201, the component retrieves a patient ECG, for example, during an ablation procedure. In block 1202, the component retrieves patient health data from the patient's EHR. In block 1203 the component retrieves the patient CT image that may have been collected during the procedure or prior to the procedure. In block 1204, the component applies a mapping system to the ECG to identify an SL. In block 1205, the component invokes the identify patient AT component to identify a patient AT based on the ECG, CT scan, patient health data, and source location. In block 1206, the component generates a PP feature vector based on the patient ECG, patient characteristics, patient CT image, source location, and AT. In block 1207, the component invokes the identify PP ML model passing the AP feature vector to identify the patient PP. In block 1208, the component outputs the PP and patient AT and then completes.

An ML model employed by the TP system may be any of a variety or combination of supervised, semi-supervised, self-supervised, unsupervised, or reinforcement learning ML models including an NN such as fully connected, convolutional, recurrent, or autoencoder neural network, a restricted Boltzmann machine, a support vector machine, a Bayesian classifier, K-means clustering, K Nearest Neighbors (KNN), transformer, recommender, and so on. When the ML model is a deep neural network, the model is trained using training data that includes features derived from data and labels corresponding to the data. For example, the data may be images of ECGs with a feature being the image itself or derived from the image (e.g., QRS integral), and the labels may be a characteristic indicated by the ECGs (e.g., AT). The training results in a set of weights for the activation functions of the layers of the deep neural network. The trained deep neural network can then be applied to new data to generate a label for that new data. When the ML model is a support vector machine, a hyper-surface is found to divide the space of possible inputs. For example, the hyper-surface attempts to divide the EHRs associated with each PP by maximizing the distance between the EHRs associated with a PP from the EHRs associated with other PPs to define the hyper-surface. The trained support vector machine can then be applied to new data to generate a classification (e.g., normal sinus rhythm or arrhythmia) for the new data. An ML model may generate values of discrete domain (e.g., classification), probabilities, and/or values of a continuous domain (e.g., regression value, classification probability).

An NN model has three major components: architecture, loss function, and search algorithm. The architecture defines the functional form relating the inputs to the outputs (in terms of network topology, unit connectivity, and activation functions). The search in weight space for a set of weights that minimizes the loss function is the training process. An NN model may use a radial basis function (RBF) network and a standard or stochastic gradient descent as the search technique with backpropagation.

A CNN has multiple layers such as a convolutional layer, a rectified linear unit (ReLU) layer, a pooling layer, a fully connected (FC) layer, and so on. Some more complex CNNs may have multiple convolutional layers, pooling layers, and FC layers. Each layer includes a neuron for each output of the layer. A neuron inputs outputs of prior layers (or original input) and applies an activation function to the inputs to generate an output.

A convolutional layer may include multiple filters (also referred to as kernels or activation functions). A filter inputs a convolutional window, for example, of a CT slice of a heart image, applies weights to each pixel of the convolutional window, and outputs a value for that convolutional window. For example, if the static image is 256 by 256 pixels, the convolutional window may be 8 by 8 pixels. The filter may apply a different weight to each of the 64 pixels in a convolutional window to generate the value. The convolutional layer may include, for each filter, a node (also referred to as a neuron) for each pixel of the CT slice assuming a stride of one with appropriate padding. Each node outputs a feature value based on a set of weights for the filter that are learned.

An activation function has a weight for each input and generates an output by combining the inputs based on the weights. The activation function may be a rectified linear unit (ReLU) that sums the values of each input times its weight to generate a weighted value and outputs max (0,weighted value) to ensure that the output is not negative. The weights of the activation functions are learned when training a ML model. The ReLU function of max (0,weighted value) may be represented as a separate ReLU layer with a neuron for each output of the prior layer that inputs that output and applies the ReLU function to generate a corresponding "rectified output."

A pooling layer may be used to reduce the size of the outputs of the prior layer by downsampling the outputs. For example, each neuron of a pooling layer may input 16 outputs of the prior layer and generate one output resulting in a 16-to-1 reduction in outputs.

An FC layer includes neurons that each input all the outputs of the prior layer and generate a weighted combination of those inputs. For example, if the penultimate layer generates 256 outputs and the FC layer inputs a neuron for each of three classifications, each neuron inputs the 256 outputs and applies weights to generate value for its classification.

Multimodal ML combines different modalities of input data to make a prediction. The modalities may be, for example, images, text, and ECGs.

In one multimodal ML approach, referred to as "early fusion," data of the different modalities is combined at the input stage and is then trained on the multimodal data. The training data for these modalities include a collection of sets of an image, related text, and related ECGs and labels. The image, text, and ECGs may be used in their original form or preprocessed, for example, to reduce its dimensionality by compressing the data into byte arrays or applying a principal component analysis. A byte array may be processed by a cross-attention mechanism to condense the bytes into a vector of a fixed size. The vectors are then used to train an ML model which may be a supervised, self-supervised, or unsupervised ML model.

In a second multimodal machine learning approach, data from different modalities may be kept separate at the input stage and used as inputs to different, modality-specific ML models (e.g., a CNN for image data, a transformer for text, and a recurrent neural network (RNN) for a voltage-time series representation of an ECG). The modality-specific ML models may be trained jointly such that information from across different modalities is combined to make predictions, and the combined (cross-modality) loss is used to adjust model weights. Alternatively, the modality-specific ML models may also be trained separately using a separate loss function for each modality. A combined ML model is then trained based on the outputs of the modality specific models. Continuing with the example, the training data for each modality-specific ML model may be based on its data along with a label. The combined ML model is then trained with the outputs of the modality-specific ML models with a final label.

Transformer machine learning was introduced as an alternative to a recurrent neural network that is both more effective and more parallelizable. (See, Vaswani, A., Shazeer, N., Parmar, N., Uszkoreit, J., Jones, L., Gomez, A. N., Kaiser, Ł. and Polosukhin, I., 2017. Attention is all you need. *Advances in neural information processing systems*, 30, which is hereby incorporated by reference.) Transformer machine learning was originally described in the context of natural language processing (NLP) but has been adapted to other applications such as image processing to augment or replace a CNN. In the following, transformer machine learning is described in the context of NLP as introduced by Vaswani.

A transformer ML model includes an encoder whose output is input to a decoder. The encoder includes an input embedding layer followed by one or more encoder attention layers. The input embedding layer generates an embedding of the inputs. For example, if a transformer ML model is used to process a sentence as described by Vaswani, each word may be represented as a token that includes an embedding of a word and its positional information. The embedding of the word is a vector representation of the word. The embeddings of the words have the characteristic that words with similar meanings are closer in the vector space. The positional information is based on the position of the word in the sentence.

The first encoder attention layer inputs the embeddings and the other encoder attention layers input the output from the prior encoder attention layer. An encoder attention layer includes a multi-head attention mechanism followed by a normalization sublayer whose output is input to a feedforward NN followed by a normalization sublayer. A multi-head attention mechanism includes multiple self-attention mechanisms that each inputs the encodings of the previous layer and weighs the relevance of each encoding to other encodings. For example, the relevance may be determined by the following attention function:

$$\text{Attention}(Q, K, V) = \text{softmax}\left(\frac{QK^T}{\sqrt{d_k}}\right)V$$

where Q represents a query, K represents a key, V represents a value, and $d_k$ represents the dimensionality of K. This attention function is referred to as scaled dot-product attention. In Vaswani, the query, key, and value of an encoder multi-head attention mechanism is set to the input of the encoder attention layer. The multi-head attention mechanism determines the multi-head attention as represented by the following:

$$\text{MultiHead}(Q,K,V) = \text{concat}(\text{head}_1, \ldots, \text{head}_8)W^o$$

$$\text{head}_i = \text{Attention}(QW_i^Q, KW_i^K, VW_i^V)$$

where W represents weights that are learned during training. The weights for the feedforward networks are also learned during training. The weights may be initialized to random values. A normalization layer normalizes its input to a vector having a dimension as expected by the next layer or sublayer.

The decoder includes an output embedding layer, decoder attention layers, a linear layer, and a softmax layer. The output embedding layer inputs the output of the decoder shifted right. Each decoder attention layer inputs the output of the prior decoder attention layer (or the output embedding layer) and the output of the encoder. The embedding layer is input to the decoder attention layer, the output of the decoder attention layer is input the linear layer, and the output of the linear layer is input to the softmax layer which outputs probabilities. A decoder attention layer includes a decoder masked multi-head attention mechanism followed by a normalization sublayer, a decoder multi-head attention mechanism followed by a normalization sublayer, and a feedforward neural network followed by a normalization sublayer. The decoder masked multi-head attention mechanism masks the input so that predictions for a position are only based on outputs for prior positions. A decoder multi-head attention mechanism inputs the normalized output of the decoder masked multi-head attention mechanism as a query and the output of the encoder as a key and a value. The feedforward neural network inputs the normalized output of the decoder multi-head attention mechanism. The normalized output of the feedforward neural network is the output of that multi-head attention layer. The weights of the linear layer are also learned during training.

After being trained, a sentence may be input to the encoder to generate an encoding of the sentence that is input to the decoder. Initially, the output of the decoder that is input to the decoder is set to null. The decoder then generates an output based on the encoding and the null input. The output of the decoder is appended to the decoder's current input, and the decoder generates a new output. This decoding process is repeated until the encoder generates a termination symbol.

Although initially developed to process sentences, transformers have been adapted for image classification. The input to a decoder of a transformer may be a representation of fixed-size patches of the image. (See, Dosovitskiy, A., Beyer, L., Kolesnikov, A., Weissenborn, D., Zhai, X., Unterthiner, T., Dehghani, M., Minderer, M., Heigold, G., Gelly, S. and Uszkoreit, J., 2020. An image is worth 16×16 words: Transformers for image recognition at scale. *arXiv preprint arXiv:*2010.11929, which is hereby incorporated by reference.) The representation of a patch may be, for each pixel of the patch, an encoding of its row, column, and color. The output of the encoder is fed into an NN to generate a classification of the image. The TP system may employ a transformer to, for example, identify a source location, target location, and/or ablation pattern given an ECG and/or identify a PP given an EHR. An EHR may be represented as key-value pairs where a key identified data type (e.g., blood pressure, heart rate, scar tissue) and a value for that data type (e.g., 160/100, 72, volume).

The TP system may also employ a state space model (SSM) to generate a latent representation of electrogram. An example of an SSM is S4 as described in Gu, A. and Dao, T., 2023. Mamba: Linear-time sequence modeling with selective state spaces. *arXiv preprint arXiv:*2312.00752 (Mamba), which is hereby incorporated by reference. Mamba provides a unique selection mechanism that adapts structured SSM parameters based on the input to selectively focus on relevant information within sequences, effectively filtering out less pertinent information. Mamba integrates SSM with multi-layer perceptron (MLP) blocks to support sequence modeling for sequential data such as cardiograms.

An unsupervised ML technique trains an ML model using unlabeled training data. K-means clustering is an example ML technique. Given feature vectors representing the training data, k-means clustering clusters the feature vectors into cluster of similar feature vectors. With k-means clustering, the number of clusters may be predefined. For example, the classification system may employ 50 clusters (k=50) to represent a cluster for each PP. An example training technique initially randomly places a feature vector (e.g., EHR data) in each cluster. The training then repeatedly calculates a mean feature vector of each cluster, selects a feature vector not in a cluster, identifies the cluster whose mean is most similar, adds the feature vector to that cluster, and moves the feature vectors already in the clusters to the cluster with the most similar mean. Similarity may be determined, for example, based on Pearson similarity, cosine similarity, and so on. The training ends when all the feature vectors have been added to a cluster. To identify a PP, a feature vector is generated based on the ECG, the cluster with a mean that is most similar to that feature vector is identified, and the ECG is assigned the classification of that cluster.

Self-supervised learning is an ML technique that is based on unlabeled training data. Initially, self-supervised learning augments the training data to generate additional training data to generate sets of training data that are similar. For example, if the training data is ECG images, the self-supervised learning generates, for each ECG image, ECG images of varied timings and voltages. An ML model may have an encoder layer, pretext task layer, and contrastive learning component. The encoder layer encodes the images into a latent vector. The pretext task layer includes weights for grouping images into different clusters based on their differences using contrastive learning. Contrastive learning component employs a loss function for contrasting the images and adjusting the weights of the encoder and the pretext task layer. This approach is similar to k-means clustering but based on contrast rather than similarity. The weights of the pretext layer can be used as initial weights of a primary task such as an AF/AFL ML model which can be trained using labeled training data. Self-supervised learning may be performed on multimodal data as described above.

An ML decision tree defines information (e.g., PP) that is associated with entities (e.g., patients) that have certain characteristics. An ML decision may have the same form as a manually generated decision tree. However, the feature associated with each decision node of an ML decision tree may be selected automatically based on analysis of the training data. Each decision node (i.e., non-leaf node) of a decision tree corresponds to a feature and each branch from a decision node may correspond to a value or range of values for the feature of that decision node. For example, a decision node corresponding to blood pressure may have branches for low, normal, high, and very high, and a decision node corresponding to heart rate may have branches for bradycardia, normal heart rate, and tachycardia. The leaf nodes of the decision tree may indicate a PP. The PP of a leaf node may be appropriate for a patient with features that match the values of the features along the path from the root node to that leaf node.

For an ML decision tree, an entropy score may be used by an ML decision tree generator to select the feature to be associated with each decision node. The entropy score, for a possible feature for a decision node, is based on the distribution of its values in node feature vectors for that node. A node feature vector for a decision node has the values of the branches along the path from the root node to that decision node. If a first possible feature for a decision node has an equal number of node feature vectors for each value, the entropy for the first possible feature is considered to be high. In contrast, if a second possible feature has node feature vectors for which 75% have the same value, then the entropy for the second possible feature is considered to be low. In such a case, the ML decision tree generator would select the second possible feature for that decision node. The ML decision tree generator may also analyze features with continuous values to identify cut points that tend to minimize entropy. For example, as mentioned above, heart rate may be categorized as bradycardia (<60), normal (60-100), or tachycardia (>100). However, since heart rate is a continuous value, the AAML system may employ techniques to identify cut points (other than 60 and 100) that would reduce the entropy. For example, a single cut point of 80 or cut points of 50 and 90 may tend to minimize entropy. Techniques for identifying cut points are described in Fayyad, U. M. and Irani, K. B., 1992. On the handling in decision tree of continuous-valued attributes generation. *Machine Learning*, 8, pp. 87-102, which is hereby incorporated by reference.

An ML decision tree generator may employ a depth-first, recursive algorithm to build the ML decision tree. The ML decision tree generator may employ a path termination criterion to determine when to terminate a path. The path termination criterion may be, for example, when the percentage of node feature vectors that are associated with the same PP is above a threshold percentage. For example, if 95% of the node feature vectors have the same PP, the ML decision tree generator may add a leaf node that indicates that 95% of cohort patients had a successful ablation using that PP. Other termination criteria may be that the number of node feature vectors is below a threshold number, or the path has reached a maximum depth. In such cases, the ML decision tree generator may add a leaf node that indicates that a PP recommendation cannot be provided or that the PP recommendation has a low confidence.

To provide recommendation for a patient, a feature vector is generated for the patient based on the patient's EHRs and/or from questions answered by the patient or medical provider. The values of the features of the patient feature vector are used to identify the path that the patient feature vector matches. The PP recommendation is based on the leaf node of that path.

In some embodiments, a KNN model provides information relating to a patient. The training data for a KNN model may be training feature vectors (e.g., EHRs) and a label for each feature vector indicating a PP. A KNN model may be used without a training phase that is without learning weights or other parameters to represent the training data. In such a case, the patient feature vector is compared to the training feature vectors to identify a number (e.g., represented by the "K" in KNN) of similar training feature vectors. Once the number of similar training feature vectors are identified, the labels associated with the similar training feature vectors are analyzed to provide information for the patient. The labels of the training feature vectors that are more similar to a patient feature vector may be given a higher weight than those that are less similar. For example, if k is 10 and four training feature vectors are very similar and six are less similar, similarity weights of 0.9 may be assigned to the very similar training feature vectors and 0.2 to the less similar. If three of the four and one of the six have the same information, then the information for the patient is primarily based on that information even though most of the 10 have different information. Conceptually, training feature vectors that are very similar are closer to the entity feature vector in a multi-dimensional space of features and a similarity weight is based on distance between the feature vectors. Various techniques may be employed to calculate a similarity metric indicating similarity between a patient feature vector and a training feature vector such as a dot product, cosine similarity, Pearson correlation, and so on.

If the number of training feature vectors is large, various techniques may be employed to effectively "compress" the training data during a training phase. For example, a clustering technique may be employed to identify clusters of training feature vectors that are similar and have the same label. A training feature vector may be generated for each cluster (e.g., one from the cluster or one based on mean values for the features) as a cluster feature vector and assign a cluster weight to it based on number of training feature vectors in the cluster.

The TP system may employ a recommender ML system to identify a PP based on clinical PPs used in successful ablations. A recommender ML system may analyze large volumes of clinician data to identify patterns aiming to curate personalized PP recommendations. By leveraging clinical data of successful ablation, the recommender ML system can offer suggestions that are tailored to data derived from a patient's EHR and data provided by a care provider. A recommender ML system may employ various ML algorithms such as collaborative filtering. Collaborative filtering focuses on finding similarities among the EHR of patients who have had successful ablations. By identifying patterns of similarity, the recommender ML system can predict how successful a PP would be for a patient. The recommender ML system may employ matrix factorization to reduce a large patient-PP matrix into lower-dimensional matrices, identifying latent factors characteristics of patients and PPs. NNs and deep learning approaches may be employed to further refine recommendations by capturing non-linear relationships and complex patterns within the data, accommodating a richer set of features such as images and the evolution of a medical condition.

The following paragraphs describe various aspects of the TP system. An implementation of the TP system may employ any combination or sub-combination of the aspects and may employ additional aspects. The processing of the aspects may be performed by one or more computing systems with one or more processors that execute computer-executable instructions that implement the aspects and that are stored on one or more computer-readable storage mediums.

In some aspects, the techniques described herein relate to a method performed by one or more computing systems for generating an ablation plan for an ablation procedure to be performed on a body part of a patient, the body part having an abnormal pattern of electrical activity. The method receives patient data of the patient that includes a patient electrogram, a patient body part image; and patient health data/The method applies an ablation target system to identify an ablation target within the body part based on at least some of the patient data. The method applies an ablation plan system to at least some of the patient data and the ablation target to identify an ablation plan that includes target parameter values for ablation device parameters for controlling an ablation device. The ablation plan system is developed based on data that includes data sets with patient data associated with an ablation plan; outputting an indication of the ablation target and the ablation plan. In some aspects, the techniques described herein relate to a method further including applying a mapping system to the patient electrogram to identify a source location of the abnormal pattern of electrical activity. In some aspects, the techniques described herein relate to a method wherein the ablation target specifies an ablation line that does not include the source location. In some aspects, the techniques described herein relate to a method wherein the ablation plan system is an ablation plan machine learning (ML) model that is trained with training data that include training data of patent data labeled with parameter values for ablation device parameters for controlling the ablation device. In some aspects, the techniques described herein relate to a method wherein the body part is a heart, the abnormal pattern of electrical activity is an arrhythmia, and the ablation procedure is to terminate the arrhythmia. In some aspects, the techniques described herein relate to a method wherein the ablation target is an ablation line that extends from a start location to an end location within the heart. In some aspects, the techniques described herein relate to a method wherein the ablation line defines a series of locations between the start location and the end location. In some aspects, the techniques described herein relate to a method wherein the patient health data includes data relating to one or more prior ablations. In some aspects, the techniques described herein relate to a method wherein the ablation plan ML model is based on a k nearest neighbor ML architecture. In some aspects, the techniques described herein relate to a method wherein the ablation plan ML model is based on a recommender ML architecture. In some aspects, the techniques described herein relate to a method wherein the ablation plan ML model is trained based on simulated data derived from simulations of cardiac electrical activity based on a simulated source location of an arrhythmia and a simulated ablation target. In some aspects, the techniques described herein relate to a method wherein a simulated cardiac image is generated based on a three-dimensional mesh that is based on a simulated cardiac geometry of a simulation. In some aspects, the techniques described herein relate to a method wherein the ablation plan ML model is trained based on clinical data derived from electronic health records. In some aspects, the techniques described herein relate to a method wherein the ablation target specifies an ablation line that does not include a source location of an arrhythmia. In some aspects, the techniques described herein relate to a method wherein the ablation plan ML model is a composite model that includes an electrogram ML sub-model that inputs an electrogram and outputs an electrogram representation of the electrogram and a cardiac image ML sub-model that inputs a cardiac image and outputs a cardiac image representation, and a final ML sub-model that inputs the electrogram representation, the cardiac image representation, and patient health data and outputs parameter values. In some aspects, the techniques described herein relate to a method wherein the electrogram ML sub-model and the cardiac image ML sub-model are convolutional neural networks and the final ML sub-model is a neural network. In some aspects, the techniques described herein relate to a method wherein the electrogram ML sub-model, cardiac image ML sub-model, and the final ML sub-model are trained using a combined loss function. In some aspects, the techniques described herein relate to a method wherein the ablation plan ML model is a recommender system. In some aspects, the techniques described herein relate to a method wherein the ablation plan ML model is based on a k-nearest neighbor algorithm. In some aspects, the techniques described herein relate to a method wherein the ablation device is a cryoablation device and wherein an ablation device parameter relates to balloon size of the ablation device. In some aspects, the techniques described herein relate to a method wherein the ablation device parameters include wattage and duration. In some aspects, the techniques described herein relate to a method further including during an ablation procedure: receiving characteristics of a prior ablation performed during that ablation procedure; applying the ablation target system and the ablation plan ML model factoring in the characteristics of the prior ablation to identify an ablation target and target parameters values for another ablation. In some aspects, the techniques described herein relate to a method further including applying an arrhythmia type ML model to a patient electrogram to identify an arrhythmia type. In some aspects, the techniques described herein relate to a method wherein the ablation target system and the ablation plan ML model are specific to the arrhythmia type. In some aspects, the techniques described herein relate to the method wherein the ablation target system and the ablation plan ML model input an arrhythmia type. In some aspects, the techniques described herein relate to a method wherein arrhythmia types include atrial fibrillation, atrial flutter and whether an atrial flutter is typical or atypical. In some aspects, the techniques described herein relate to a method wherein the ablation target specifies an ablation pattern.

In some aspects, the techniques described herein relate to a method performed by one or more computing systems for generating a patient ablation target for an ablation procedure to be performed on heart of a patient to treat an arrhythmia. The method receives patient data of the patient that includes a patient electrogram. The method applies an ablation target machine learning (ML) model to a patient feature vector with a patient feature based on the patient electrogram to identify the patient ablation target. The ablation target ML model is trained using training data sets that include a training feature vector with a training feature based on a training electrogram labeled with a training ablation target for a training arrhythmia. The patient ablation target and the training ablation targets specify ablation locations that do not include a source location of an arrhythmia. The method outputs an indication of the patient ablation target. In some aspects, the techniques described herein relate to a method wherein the patient feature vector includes a patient feature that is a patient source location of a patient arrhythmia and each training data feature vector including a training feature that is a training source location of a training arrhythmia. In some aspects, the techniques described herein relate to a method wherein the patient feature vector includes a patient feature that is a patient cardiac image and each training feature vector include a training feature that is a training cardiac image. In some aspects, the techniques described herein relate to a method wherein the patient ablation target is an ablation line that extends from a start location to an end location within the heart. In some aspects, the techniques described herein relate to a method wherein the ablation line defines a series of locations between the start location and the end location. In some aspects, the techniques described herein relate to a method wherein the patient feature vector includes a patient feature derived from a prior ablation performed on the patient. In some aspects, the techniques described herein relate to a method wherein the prior ablation is a pulmonary vein isolation. In some aspects, the techniques described herein relate to a method wherein the pulmonary vein isolation was performed during the ablation procedure.

In some aspects, the techniques described herein relate to a method performed by one or more computing systems for generating a patient ablation plan for an ablation procedure to be performed on the heart of a patient. The method receives patient data of the patient that includes a patient electrogram. The method applies an ablation plan machine learning (ML) model to a patient feature vector with a patient feature based on the patient electrogram to identify the patient ablation plan. The ablation plan ML model is trained using training data that includes training data sets that include training feature vectors with a training feature based on a training electrogram labeled with a training ablation plan for a training arrhythmia. The training ablation plan specifies parameter values for ablation device parameters of an ablation device; and outputting an indication of the patient ablation plan. In some aspects, the techniques described herein relate to a method wherein the patient feature vector includes a patient feature that is a patient source location of a patient arrhythmia, and each training data set includes a training feature that is a training source location of a training arrhythmia. In some aspects, the techniques described herein relate to a method wherein the patient feature vector includes a patient feature that is a patient cardiac image, and each training data set includes a training feature that is a training cardiac image. In some aspects, the techniques described herein relate to a method wherein the patient feature vector includes a patient feature that is a patient ablation target, and each training data set includes a training feature that is a training ablation target. In some aspects, the techniques described herein relate to a method wherein patient ablation plan further specifies a patient ablation target. In some aspects, the techniques described herein relate to a method wherein the patient feature vector further includes a feature based on a prior ablation performed on the patient. In some aspects, the techniques described herein relate to a method wherein the prior ablation is a pulmonary vein isolation.

In some aspects, the techniques described herein relate to one or more computing systems for generating an ablation target machine learning (ML) model, the one or more computing systems includes one or more computer-readable storage mediums that store computer-executable instructions for controlling the one or more computing systems. The instructions, for each of a plurality of training cardiac images, generate a 3D mesh based on that training cardiac image. The instructions access one or more of training health record data sets. For each of a plurality of combinations of a 3D mesh and a training health record data set and for each of a plurality of combinations of a simulated source location of a simulated arrhythmia and a simulated ablation target that is not the simulated source location, the instructions run a simulation of cardiac electrical activity using that 3D mesh, that training health data set, that simulated source location, and that simulated ablation target. The instructions that run the simulation run an initial portion of the simulation that is not based on the simulated ablation target until the simulated arrhythmia is induced and then run a final portion of the simulation that is based on the simulated ablation target to determine whether an ablation performed based on that simulated ablation target would terminate a simulated arrhythmia originating from that simulated source location. The instructions, when the simulation indicates that the simulated arrhythmia would be terminated, generate a simulated electrogram based on the simulated cardiac electrical activity of the initial portion and generate a training data set that includes that simulated electrogram, that training cardiac image on which that 3D mesh was based on, and that training health data set labeled with that simulated ablation target. The instructions train the ablation target ML model using the training data sets. The one or more computing systems include one or more processors for executing one or more of the computer-executable instructions. In some aspects, the techniques described herein relate to one or more computing systems wherein the computer-executable instructions further include instructions to apply the ablation target ML model to a patient electrogram, a patient cardiac image, and a patient health data set of a patient to determine a patient ablation target for treating the patient.

All documents incorporated by reference are incorporated in their entirety for the full extent of their disclosures. In the event of inconsistencies between the language in this document and any incorporated-by-reference document, the language in the incorporated-by-reference document should be considered supplementary to that of this document and the language in this document controls.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

We claim:

1. A method performed by one or more computing systems for generating an ablation plan for an ablation procedure to be performed on a patient heart of a patient, the patient heart having a patient arrhythmia, the ablation plan specifying a patient ablation target and a patient parameter plan for treating the patient arrhythmia, the method comprising:

receiving patient data of the patient that includes a patient electrogram and a patient heart image;

identifying a patient source location of the patient arrhythmia based on the patient electrogram;

applying an ablation target system to identify the patient ablation target within the patient heart based on at least some of the patient data and the patient source location, wherein the ablation target system identifies the patient ablation target based on similarity of the patient electrogram to mappings of simulated electrograms and simulated ablation targets of a plurality of persons already treated, wherein the mappings of the stimulated electrograms are generated by a plurality of combinations of a simulated source location of a simulated arrhythmia and a simulated ablation target for each of the plurality of persons already treated;

running a simulation of electrical activity of at least one person's heart of the plurality of persons already treated using a three-dimensional (3D) mesh representing the at least one person's heart that is derived from the at least one person's heart image, wherein an initial portion of the simulation of the electrical activity of the at least one person's heart is run, based on the simulated source location and not based on the simulated ablation target, until a simulated arrhythmia is induced, and a final portion of the simulation of the electrical activity of the at least one person's heart is run, based on the simulated ablation target, to determine whether an ablation performed on the at least one person's heart targeting the simulated ablation target would terminate the simulated arrhythmia originating from the simulated source location;

applying a parameter plan system to at least some of the patient data and the patient ablation target to identify the patient parameter plan that includes parameter values for tunable parameters of an ablation device for controlling the ablation device, the patient parameter plan developed based on, the plurality of the persons already treated, a person ablation target and a person parameter plan for each of the plurality of persons already treated that were successful in treating an arrhythmia; and outputting an indication of the patient ablation target and the patient parameter plan.

2. The method of claim 1 wherein the identifying of the patient source location includes applying a mapping system to the patient electrogram to identify the patient source location of the patient arrhythmia.

3. The method of claim 2 wherein the patient ablation target specifies an ablation line that does not include the patient source location.

4. The method of claim 1 wherein the parameter plan system is a parameter plan machine learning (ML) model that is trained with training data that includes, for each person of the plurality of persons already treated which the parameter plan system is based on.

5. The method of claim 4 wherein the parameter plan ML model is based on a K-nearest neighbor ML architecture.

6. The method of claim 4 wherein the parameter plan ML model is based on a recommender ML architecture.

7. The method of claim 4 wherein the ablation device is a cryoablation device and wherein a tunable parameter relates to balloon size of the ablation device.

8. The method of claim 4 wherein the tunable parameters include wattage and pulse duration.

9. The method of claim 1 wherein the tunable parameters include one or more of wattage, current, frequency, pulse shape, pulse duration, pulse frequency, and contact force.

10. The method of claim 1 wherein the tunable parameters include one or more of balloon size, electrode size and spacing, electrode orientation, impedance, hoop diameter, and fluence of the ablation device.

11. A method performed by one or more computing systems for generating an ablation plan for an ablation procedure to be performed on a body part of a patient, the body part having an abnormal pattern of electrical activity, the method comprising:

receiving patient data of the patient that includes a patient electrogram and a patient body part image;

applying a mapping system to the patient electrogram to identify a source location of the abnormal pattern of electrical activity;

applying an ablation target system to identify an ablation target within the body part based on at least some of the patient data;

applying a parameter plan system to at least some of the patient data and the ablation target to identify an ablation plan that includes target parameter values for ablation device parameters for controlling an ablation device, the parameter plan system developed based on data that includes clinical data sets that are each derived from an electronic health record of a person of a plurality of persons already treated, each clinical data set associated with a person parameter plan of the person; and outputting an indication of the ablation target and the ablation plan;

wherein the body part is a heart, the abnormal pattern of electrical activity is an arrhythmia, and the ablation procedure is to terminate the arrhythmia;

wherein the parameter plan system is a parameter plan machine learning (ML) model that is trained with training data that includes data of clinical data sets labeled with parameters values for ablation device parameters for controlling the ablation device; and wherein the parameter plan ML model is a composite model that includes an electrogram ML sub-model that inputs the patient electrogram of the patient and outputs a patient electrogram representation of the patient electrogram and includes a cardiac image ML sub-model that inputs a patient cardiac image of the patient and outputs a patient cardiac image representation, and a final ML sub-model that inputs the patient electrogram representation and the patient cardiac image representation and outputs parameter values.

12. The method of claim 11 wherein the electrogram ML sub-model and the cardiac image ML sub-model are convolutional neural networks and the final ML sub-model is a neural network.

13. The method of claim 12 wherein the electrogram ML sub-model, cardiac image ML sub-model, and the final ML sub-model are trained using a combined loss function.

14. A computing system for generating an ablation plan for a patient ablation procedure to be performed on a patient heart of a patient who has a patient arrhythmia, the computing system comprising:

one or more computer-readable storage mediums configured to store a person data for each of a plurality of persons already treated who have had a person ablation procedure to treat a person arrhythmia, the person data including a person parameter plan, a person cardiogram, and a person ablation target, the person parameter plan including person parameter values for tunable parameters of an ablation device; and computer-executable instructions for controlling the computing system programmed to:

access patient data of the patient that includes a patient cardiogram;

identify a patient source location of the patient arrhythmia based on the patient cardiogram;

apply an ablation target system to identify, based on the patient source location and the patient data, a patient ablation target within the patient heart, the ablation target system based on a plurality of combinations of a simulated source location of a simulated arrhythmia and a simulated ablation target of each of the plurality of the persons already treated, running a simulation of electrical activity of at least one person's heart of the plurality of persons already treated using a three-dimensional (3D) mesh representing the at least one person's heart that is derived from the person data of the at least one person,
an initial portion of the simulation being run, based on the simulated source location and not based on the simulated ablation target, until the simulated arrhythmia is induced, and
a final portion of the simulation being run, based on the simulated ablation target, to determine whether an ablation performed targeting the simulated ablation target would terminate the simulated arrhythmia originating from the simulated source location;
apply a parameter plan system to the patient data and the patient ablation target to identify a patient parameter plan that includes patient parameter values for tunable parameters of a patient ablation device for controlling the patient ablation device, the patient parameter plan developed based on the person data of each of the plurality of persons already treated who have had a successful person ablation procedure to treat the person arrhythmia;
send to the patient ablation device the patient ablation target and the patient parameter plan; and
direct the performing of the patient ablation procedure on the patient based on the patient ablation target and the patient parameter plan; and
one or more processors for controlling the computing system to execute the computer-executable instructions.

15. The computing system of claim 14 further comprising computer-executable instructions to train a parameter plan machine learning (ML) model with training data that includes feature vectors and labels, a feature vector having features derived from the person data of at least one person of the plurality of persons already treated and the person ablation target location of the at least one person, a label indicating a person parameter plan of the at least one person, wherein the parameter plan system employs the parameter plan ML model to identify the patient parameter plan.

16. The computing system of claim 15 wherein the person data further includes a person cardiac image of the at least one person of the plurality of persons already treated and wherein the feature vector includes a feature derived from the person cardiac image of the at least one person.

17. The computing system of claim 15 wherein one or more features are derived from one or more of cardiac chambers of a person heart of at least one person of the plurality of persons already treated associated with the person arrhythmia and a person arrhythmia type, a person flutter type, a person prior ablation, and person scar tissue characteristics of the at least one person.

18. The computing system of claim 14 wherein the tunable parameters include one or more of wattage, current, frequency, pulse shape, pulse duration, pulse frequency, or contact force.

19. A method for treating a patient based on an ablation plan for an ablation procedure to be performed on a patient heart of the patient, the patient heart having a patient arrhythmia, the ablation plan specifying a patient ablation target and a patient parameter plan for treating the patient arrhythmia, the method comprising:
receiving patient data of the patient that includes a patient electrogram and a patient heart image;
identifying a patient source location of the patient arrhythmia based on the patient electrogram;
applying an ablation target system to identify the patient ablation target within the patient heart based on at least some of the patient data and the patient source location, wherein the ablation target system identifies the patient ablation target based on similarity of the patient electrogram to mappings of simulated electrograms and simulated ablation targets of a plurality of persons already treated, wherein the mappings of simulated electrograms are generated by a plurality of combinations of a simulated source location of a simulated arrhythmia and a simulated ablation target for each of the plurality of persons already treated;
running a simulation of electrical activity of at least one person's heart of the plurality of persons already treated using a three-dimensional (3D) mesh representing the at least one person's heart that is derived from the at least one person's heart image, wherein:
an initial portion of the simulation of the electrical activity of the at least one person's heart is run, based on the simulated source location and not based on the simulated ablation target, until a simulated arrhythmia is induced, and
a final portion of the simulation of the electrical activity of the at least one person's heart is run, based on the simulated ablation target, to determine whether an ablation performed on the at least one person's heart targeting the simulated ablation target would terminate the simulated arrhythmia originating from the simulated source location;
applying a parameter plan system to at least some of the patient data and the patient ablation target to identify the patient parameter plan that includes parameter values for tunable parameters of an ablation device for controlling the ablation device, the patient parameter plan developed based on person data of the at least one person of the plurality of persons already treated, the person data of the at least one person including a person ablation target and a person parameter plan for the at least one person of the plurality of persons already treated that were successful in treating an arrhythmia; and
performing the ablation procedure on the patient based on the patient ablation target and the patient parameter plan.

* * * * *